United States Patent [19]

Karapetian et al.

[11] 4,035,429
[45] July 12, 1977

[54] METHOD OF PRODUCING 2,3-DICHLORBUTADIENE-1,3

[76] Inventors: Norair Gareginovich Karapetian, ulitsa Barekamutian, 2, kv. 50; Gurgen Mambreevich Mkrian, ulitsa Moskovian, 28, kv. 91; Oganes Avetisovich Tonoian, ulitsa Moskovian, 28, kv. 161; Mikhail Eremovich Selimian, ulitsa Teriana, 2"b", kv. 58; Nargiz Akopovna Papazian, ulitsa Moskovian, 28, kv. 91; Rima Azarapetovna Kazarian, ulitsa Kalinina, 15/8; Anatoly Ivanovich Petrov, 3 uchastok, 7, kv. 59; Armen Alexandrovich Bakhtamian, ulitsa Moskovian, 28, kv. 98; Smbat Mirakovich Mirakian, ulitsa Shakhverdiana, 23, kv. 12, all of Erevan, U.S.S.R.

[21] Appl. No.: 223,289

[22] Filed: Feb. 3, 1972

[51] Int. Cl.$^2$ .......................................... C07C 21/20
[52] U.S. Cl. ........................ 260/655; 260/652.5 P
[58] Field of Search ........................ 260/655, 654 D

[56] References Cited

U.S. PATENT DOCUMENTS

| 1,965,369 | 7/1934 | Carothers et al. | 260/655 |
| 1,998,442 | 4/1935 | Carothers et al. | 260/655 |
| 2,610,214 | 9/1952 | Amos | 260/654 D |

FOREIGN PATENT DOCUMENTS

| 985,070 | 3/1965 | United Kingdom | 260/655 |
| 1,084,742 | 9/1967 | United Kingdom | 260/655 |

*Primary Examiner*—Delbert E. Gantz
*Assistant Examiner*—Joseph A. Boska

[57] ABSTRACT

A method of producing 2,3-dichlorobutadiene-1,3 comprising dehydrohalogenation of 2,3,4-trichlorobutene-1 with liquid ammonia in the presence of a polymerization inhibitor at a molar ratio of 2,3,4-trichlorobutene-1 to ammonia of 1:1-15 respectively at a temperature selected within the range of from −35° to +20° C under a pressure of 1–8 atm.

The method of the present invention can be performed continuously. The method makes it possible to obviate polymerization of the desired product and formation of undesirable by-products.

2 Claims, No Drawings

METHOD OF PRODUCING 2,3-DICHLORBUTADIENE-1,3

The present invention relates to methods of producing 2,3-dichlorobutadiene-1,3 which is useful as a co-monomer in the producton of chloroprene rubbers and latices.

Known in the art are methods of producing 2,3-dichlorobutadiene-1,3, for instance, by dehydrohalogenation of 1,2,3,4-tetrachlorobutane with gaseous ammonia in a polar solvent such as dimethylsulfoxide at a temperature within the range of 60°–80° C and under a pressure of 3.5–10.6 atm. in the presence of a polymerization inhibitor such as diphenylamine (cf.Bundesrepublik Deutschland Pat. No. 1,213,396 Cl.120, 19/02). Said dehydrohalogenation process is performed as follows.

Intermediate products, viz. 2,3,4-trichlorobutene-1 (I) and 1,3,4-trichlorobutene-2 (II) are obtained from the starting 1,2,3,4-tetrachlorobutane with splitting off one molecule of hydrogen chloride. The process may be represented by the following equation:

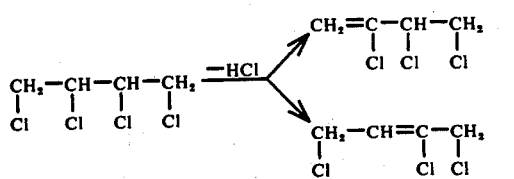

2,3-dichlorobutadiene-1,3 is formed only from the product (I) with splitting off another molecule of hydrogen chloride. The process may be schematically represented by the following equation:

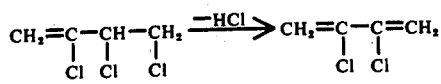

The product (II) containing an active chlorine atom (which is characteristic for halide derivatives of allyl chloride type) when further reacted with ammonia gives a complex mixture of amino derivatives. Therefore, using this known method many by-products are produced along with the desired product.

In addition, rather elevated temperatures (of the order of 60°–80° C) at which the dehydrohalogenation process is conducted contribute to polymerization of 2,3-dichlorobutadiene-1,3 which belongs to the group of extremely readily polymerizable monomers (polymerization rate of 2,3-dichlorobutadiene-1,3 is 2,000 times higher than of isoprene and considerably increased upon heating above 20° C).

It should be also noted that the dehydrohalogenation is carried out in a heterogeneous medium which does not make it possible to perform the process continuously.

The above-mentioned disadvantages result in a low yield of the desired product, namely 2,3-dichlorobutadiene-1,3.

It is an object of the present invention to provide for a method of producing 2,3-dichlorobutadiene-1,3 which can be performed continuously.

It is another object of the present invention to provide for a method of producing 2,3-dichlorobutadiene-1,3 from another starting product which would make it possible to prevent polymerization of the desired product from and formation of undesirable by-products.

These and other objects are accomplished in accordance with the present invention in that the dehydrohalogenation of 2,3,4-trichlorobutene-1 is effected with ammonia at a molar ratio of the reagents of 1:1–15 respectively at a temperature of from −35° to +20° C and under a pressure of 1–8 atm.

It is advisable to conduct the dehydrohalogenation of 2,3, 4-trichlorobutene-1 at a temperature within the range of from −15° to −17° C under a pressure of 2.3 atm. at a molar ratio of 2,3,4-trichlorobutene-1 to ammonia of 1:10–15 respectively.

Liquid ammonia is a good solvent for the starting 2,3,4-trichlorobutene-1 as well as for the resulting products (2,3-dichlorobutadiene-1,3 and ammonium chloride); i.e., in this case the reaction medium is homogeneous. This enables performing the process continuously (liquid ammonia serves both as a reagent and a solvent in the hehydrohalogenation process).

In addition, the employment of the above-mentioned temperatures for the dehydrohalogenation process makes it possible to obviate polymerization of 2,3-dichlorobutadiene-1,3 and formation of by-products.

The starting 2,3,4-trichlorobutene-1 is, in turn, produced by chlorination of 1,3-dichlorobutene-2 which is a by-product in the production of chloroprene. Accordingly, the method of the present invention solves the problem of profitable utilization of 1,3-dichlorobutadiene-2 combined with the formation of 2,3-dichlorobutadiene-1,3 which is useful in chloroprene rubber production.

The method of producing 2,3-dichlorobutadiene-1,3 according to the present invention is performed continuously in the following manner.

2,3,4-trichlorobutene-1 is subjected to dehydrochlorination in a steel column-type reactor with continuous feed of liquid ammonia to the top of the column along with 2,3,4-trichlorobutene-1 mixed with a polymerization inhibitor. As the inhibitor there may be used, diethylhydroxylamine and other compounds containing amino groups. The reagents are supplied at a molar ratio of 2,3,4-trichlorobutene-1 to ammonia of 1:1–15 respectively and preferably 1:10–1:15. The reactor temperature is maintained within the range of −35° to +20° C.

The resulting dehydrohalogenation mixture which is a solution of 2,3-dichlorobutadiene-1,3, unreacted 2,3,4-trichlorobutene-1 and ammonium chloride in liquid ammonia is evacuated from the bottom of the reactor and fed into a water spray column for dissolving excessive amounts of ammonia and ammonium chloride. Thereafter the mixture is fed into a separator wherein it is stratified into two layers: an aqueous layer and an oily one. The oily layer comprising 2,3-dichlorobutadiene-1,3 and unreacted 2,3,4-trichlorobutene-1 is evacuated from the bottom section of the separator, again washed with water until complete elimination of ammonia, and vacuum distilled, after drying, under residual pressure of 80 mm Hg. To stabilize the 2,3-dichlorobutadiene-1,3 nitrogen oxide is admitted into the rectification column in an amount of 0.03–0.05% whereas the still of the column is supplied with n-isobutylcatechol or diethylhydroxylamine in an amount of 0.5–1% by weight of the oily layer. Rectified dichlorobutadiene is stabilized with 0.05–0.1% of nitrasodiphenylamine and stored at a temperature within the range of from −10° to −5° C.

Unreacted 2,3,4-trichlorobutene-1 is recycled back to the process. From the aqueous layer (an aqueous solution of ammonium chloride and ammonia) evacuated from the top section of the reactor, ammonia is recovered by conventional techniques such as evaporation followed by condensation, dried to a water content of 0.3–1% and recycled back to the process. The ammonium chloride solution containing up to 1% of ammonia may be employed for the production of ammonium chloride.

The method of producing 2,3-dichlorobutadiene-1,3 in accordance with the present invention is further illustrated by the following examples of its embodiment.

EXAMPLE 1

Into a reactor cooled with a mixture of acetone and solidified carbon dioxide, 600 g. of liquid ammonia were poured and a mixture of 478.5 g. of 2,3,4-trichlorobutene-1 and 5 g. of beta-naphthylamine was added thereto with stirring at a temperature of from $-40°$ to $-35°$ C. The resulting homogeneous solution was retained in the reactor for a period of 12 hours at a temperature of $-35°$ to $-33°$ C under atmospheric pressure, whereafter an excess of liquid ammonia was removed by evaporation followed by condensation for reuse. To the mixture of 2,3-dichlorobutadiene-1,3, ammonium chloride and unreacted 2,3,4-trichlorobutene-1 (no polymers) remaining in the reactor, water was added until the ammonium chloride was completely dissolved. The aqueous layer was then separated from the oily one. Ammonium chloride was isolated almost quantitatively from said aqueous layer by evaporation. A mixture of chlorides (the oily layer) after drying over calcium chloride and stabilizing with 1% based on the weight of the oily layer of isobutylcatechol or nitrosodiphenylamine, was vacuum distilled under a residual pressure of 80 mm Hg to yield 265.8 g. of 2, 3-dichlorobutadiene-1,3 (b.p. $40°$–$42°$ C under 80 mm Hg, $n_D^{20}=1.4880$; $d_4^{20}=1.1810$) and 99.1 g. of unreacted 2,3,4-trichlrobutene-1 which can be repeatedly employed in the process. The conversion level of 2,3,4-trichlorobutene-1 was about 80%. The yield of 2,3-dichlorobutadiene-1,3 was 88.7% based on the 2,3,4-trichlorobutene-1 consumed in the reaction. A chromatogram of the dichlorobutadiene obtained with "Tsvet" chromatograph revealed one peak illustrating the purity of the resulting product.

EXAMPLE 2

2,3-dichlorobutadiene-1,3 was obtained by a procedure similar to that described in Example 1 with the only difference that the reaction mixture was retained in the reactor under the same temperature and pressure conditions for a period of 24 hours. As a result, 336.5 g. of 2,3-dichlorobutadiene-1,3 were obtained. The yield of the desired product was 91.2% based on the reacted 2,3,4-trichlorobutene-1.

EXAMPLE 3

Into a reactor provided with a stirrer and reflux condenser 9 kg. of liquid ammonia and a mixture of 16 kg. of 2,3,4-trichlorobutene-1 and 45 g. of diethylhydroxylamine were charged. The resulting reaction mass was stirred over a period of 3 hours at a temperature within the range of from $-5°$ to $-10°$ C under a pressure of 3–4 atm. On completion of the reaction the excess of ammonia was evaporated, condensed and drained from the reactor into a collector. To the mixture remaining in the reactor water was added until complete solution of the ammonium chloride. The oily layer was separated from the aqueous one and after drying using calcium chloride was vacuum distilled under residual pressure of 80 mm Hg to yield 10.1 kg. of 2,3-dichlorobutadiene-1,3 and 8 kg. of unreacted 2,3,4-trichlorobutene-1. The conversion level of 2,3,4-trichlorobutene-1 was 88%. The yield of 2,3-dichlorobutadiene-1,3 was 91.8% based on the reacted 2, 3,4-trichlorobutene-1.

EXAMPLE 4

The process was performed continuously. Into the upper part of a 0.5 m$^3$ cylinder-type reactor provided with a stirrer and cooling jacket, 10 kg./hr of 2,3,4-trichlorobutene-1 containing beta-phenylnaphthylamine in the amount of 2% by weight based on the trichlorobutene, and 20 kg./hr of liquid ammonia were charged. The reaction temperature was maintained within the range of from $-15°$ to $-20°$ C; the process was conducted under a pressure of 2–3 atm. The residence time of 2,3,4-trichlorobutene-1 in the reactor was 10 hours. To remove the reaction heat a liquid cooling agent was circulated in the cooling jacket at the temperature of $-30°$ C.

A solution of 2,3-dichlorobutadiene-1,3, unreacted 2, 3,4-trichlorobutene-1 and ammonium chloride in liquid ammonia was delivered from the bottom section of the reactor into a water spray column. The mixture was passed therefrom to a separator, wherein it was stratified into two layers. The upper layer was an aquous solution of ammonia and ammonium chloride, while the lower layer comprised a mixture of 2,3-dichlorobutadiene-1,3 and 2,3,4-trichlorobutene-1. Ammonia was evaporated from the upper layer, condensed and dried to a water content of 0.3–0.4% and then recycled back to the process. The lower oily layer was drained from the bottom section of the separator, washed in a spray water column to completely eliminate ammonia and after drying with calcium chloride was distilled in vacuum under a residual pressure of 80 mm Hg. To stabilize 2,3-dichlorobutadiene-1,3 upon rectification, nitrogen oxide was admitted into the column in the amount of 0.05% while the still of the column was supplied with diethylhydroxylamine in an amount of 0.5–1% by weight of the oily layer. Rectified dichlorobutadiene was stabilized with 0.1% of nitrosodiphenylamine and stored at a temperature of $-10°$ to $-5°$ C. The unreacted 2,3,4-trichlorobutene-1 was recycled to the process.

On rectification of a crude product obtained during 40 hours run of the reactor under the above-mentioned conditions, from 400 kg. of the starting 2,3,4-trichlorobutene-1 there were isolated 145.2 kg. of 2,3-dichlorobutadiene-1,3 (b.p. $40°$–$42°$ C under 80 mm Hg, $n_D^{20}=1.4880$, $d_4^{20}=1.1810$) and 191.9 kg. of unreacted 2,3,4-trichlorobutene-1 (b.p. $95°$–$100°$ C under 100 mm Hg.). The conversion level of 2,3,4-trichlorobutene-1 was 52.3%, The yield of 2,3-dichlorobutadiene-1,3 was 90.1% based on the reacted 2,3,4-trichlorobutene-1.

EXAMPLE 5

The procedure of preparing 2,3-dichlorobutadiene-1,3 according to Example 4 was repeated with the only exception that the reaction temperature was maintained within the range of from 0° to 5° C under a pressure of 4-5 atm.

When rectifying a crude product obtained during 20 hours run of the unit under said conditions, from 200 kg. of the starting 2,3,4-trichlorobutene-1 there were isolated 105.6 kg. of 2,3-dichlorobutadiene-1,3 and 45 kg. of unreacted 2,3,4-trichlorobutene-1. The conversion level of 2,3,4-trichlorobutene-1 was 77.5%. The yield of 2,3-dichlorobutadiene-1 was 86.4 based on the reacted 2,3,4-trichlorobutene-1.

EXAMPLE 6

The procedure of Example 4 for preparing 2,3-dichlorobutadiene-1,3 was followed with the only exception that the reactor was supplied with 100 kg/hr of 2,3,4-trichlorobutene-1 and 180 kg/hr of liquid ammonia. The reaction temperature was maintained within the range of from +15° to +18° C under a pressure of 7-8 atm. Residence time of the 2,3,4-trichlorobutene-1 in the reactor was 1 hour.

When rectifying a crude product obtained during 7 hours run of the unit under the above-mentioned conditions from 700 kg of the starting 2,3,4-trichlorobutene-1 there were isolated 202.5 kg. of 2,3-dichlorobutadiene-1,3 and 372.4 kg of unreacted 2,3,4-trichlorobutene-1. The conversion level of 2,3,4-trichlorobutene-1 was 46.8%. The yield of 2,3-dichlorobutadiene-1,3 was 82.2% based on the reacted 2,3,4-trichlorobutene-1.

We claim:

1. A method of producing 2,3-dichlorobutadiene-1,3 comprising dehydrohalogenation of 2,3,4-trichlorobutene-1 with liquid ammonia in the presence of a polymerization inhibitor at a molar ratio of 2,3,4-trichlorobutene-1 to ammonia of 1:1-15 respectively at a temperature within the range of from −35° to +20° C under a pressure of 1-8 atm.

2. A method as claimed in claim 1, wherein the dehydrohalogenation of 2,3,4-trichlorobutene-1 is effected at a temperature within the range of from −15° to −17° C under a pressure of 2-3 atm. at a molar ratio of 2,3,4-trichlorobutene-1 to ammonia of 1:10-15 respectively.

* * * * *